United States Patent
Nix et al.

[19]

[11] Patent Number: 6,138,497
[45] Date of Patent: Oct. 31, 2000

[54] METHOD AND APPARATUS FOR SIMULTANEOUSLY MEASURING $CO_2$, $O_2$ AND $N_2$ DISSOLVED IN LIQUID

[75] Inventors: John A. Nix, Atlanta; Robert A. Wilks, Norcross, both of Ga.; Richard E. Kugler, Essen, Germany; Leonard E. Henry, Jr., Kingston, Ga.

[73] Assignee: The Coca-Cola Company, Atlanta, Ga.

[21] Appl. No.: 08/323,660

[22] Filed: Oct. 17, 1994

[51] Int. Cl.[7] ................................................. G01N 7/02
[52] U.S. Cl. .................. 73/19.06; 73/19.1; 73/19.05; 250/339.13
[58] Field of Search ............................. 73/19.01, 19.05, 73/19.06, 19.1, 24.02, 52, 863.33; 250/343, 339.13, 364, 365, 361 R, 361 C

[56] References Cited

U.S. PATENT DOCUMENTS

| | | | |
|---|---|---|---|
| 3,539,804 | 11/1970 | Billetdeaux et al. | 250/339.13 X |
| 3,612,866 | 10/1971 | Stevens | 250/71 |
| 3,673,853 | 7/1972 | Griswold et al. | 73/19.1 |
| 3,725,658 | 4/1973 | Stanley et al. | 250/364 |
| 4,120,192 | 10/1978 | Williamson | 73/19.1 |
| 4,810,655 | 3/1989 | Khalil et al. | 436/172 X |
| 5,043,285 | 8/1991 | Surgi | 436/136 |
| 5,108,932 | 4/1992 | Wolfbeis | 436/124 |
| 5,365,771 | 11/1994 | Gysi et al. | 73/863.33 |
| 5,426,593 | 6/1995 | Seiden et al. | 73/19.01 X |
| 5,440,927 | 8/1995 | Chu et al. | 250/365 |

OTHER PUBLICATIONS

"Evaluation of Some Immobilized Room–Temperature Phosphorescent Metal Chelates as Sensing Materials for Oxygen" by Yi–Ming Liu et al, Analytical Chemistry, vol. 66, No. 6, Mar. 1994.

*Primary Examiner*—Hezron Williams
*Attorney, Agent, or Firm*—Finnegan, Henderson, Farabow, Garrett & Dunner, L.L.P.

[57] ABSTRACT

A method for simultaneously measuring $CO_2$, $O_2$ and $N_2$ gases dissolved in liquid includes a device for extracting the sample of gases from a container, such as a soft drink bottle, and a gas sample cell connected in fluid communication with the gas extracting device. The concentrations of $CO_2$ and $O_2$ gas in the gas sample are determined utilizing infrared (IR) absorption and phosphorescent quenching, respectively. The concentration of these respective gases is then converted to a partial pressure reading utilizing the temperature of the gas sample. The partial pressure of nitrogen gas in the sample is determined by measuring the total pressure of the gas sample and subtracting the partial pressures of the $CO_2$ and $O_2$ gas therefrom. The respective partial pressures of the $CO_2$, $O_2$ and $N_2$ gases are then converted to concentration of those gases in the liquid sample in the soft drink bottle, as a function of their solubility values at the temperature of the gas sample.

8 Claims, 3 Drawing Sheets

METHOD AND APPARATUS FOR SIMULTANEOUSLY MEASURING $CO_2$, $O_2$ AND $N_2$ DISSOLVED IN LIQUID

BACKGROUND OF THE INVENTION

The present invention relates to a method for determining amounts of $CO_2$ (carbon dioxide), $O_2$ (oxygen) and $N_2$ (nitrogen) gases dissolved in a liquid sample and an apparatus for performing the method. More specifically, the present invention relates to a method and apparatus for extracting a sample of gases dissolved in a liquid and measuring the gas sample extracted for quantities of the respective $CO_2$, $O_2$ and $N_2$ gases and determining their concentrations in the liquid from known solubility values.

In order to achieve good quality control carbonated beverages in either bottling plants or trade sample laboratories, it is necessary to measure the concentrations of carbon dioxide, oxygen and nitrogen gases dissolved in liquid solutions. These are the primary gases of interest when evaluating the quality of carbonated soft drinks. Generally, the commercial techniques presently known to measure any one of these gases are slow, expensive, inaccurate, or simply not suitable for use in bottling plants or trade sample laboratories.

Accordingly, a need in the art exists for an improved technique to simultaneously measure the concentrations of ($CO_2$) carbon dioxide, ($O_2$) oxygen, and ($N_2$) nitrogen gases dissolved in liquid solutions such as carbonated soft drinks.

SUMMARY OF THE INVENTION

Accordingly, it is a primary object of the present invention to provide a method for determining amounts of $CO_2$, $O_2$ and $N_2$ gases dissolved in a liquid sample substantially simultaneously.

It is another object of the present invention to provide an apparatus for performing this method which is relatively compact and inexpensive.

It is still another object of the present invention to provide a system in which the apparatus of the present invention may be utilized to test the concentrations of gases in a plurality of soft drink containers in an efficient manner.

The objects of the present invention are fulfilled in part by providing a method for determining amounts of $CO_2$, $O_2$ and $N_2$ gases dissolved in a liquid sample substantially simultaneously comprising the steps of:

a) extracting a gas sample from the liquid sample;
b) measuring the concentration of $CO_2$ gas in the extracted gas sample;
c) measuring the concentration of $O_2$ gas in the gas sample;
d) measuring the total pressure of the gas sample;
e) measuring the temperature of the gas sample;
f) calculating the partial pressure of $CO_2$ gas from the concentration measured in step b) and the temperature measured in step e);
g) calculating the partial pressure of $O_2$ gas from the concentration measured in step c) and the temperature measured in step e);
h) subtracting the sum of the partial pressures of $CO_2$ and $O_2$ determined in steps f) and g) from the total pressure determined in step c) to determine the partial pressure of $N_2$; and
i) determining the concentration of $CO_2$, $O_2$ and $N_2$ gases dissolved in the liquid sample from the respective partial pressures determined in steps f), g) and h) and the temperature determined in step e).

The concentration of $CO_2$ in the extracted gas sample is determined by transmitting infrared (IR) radiation of wavelengths which will be absorbed by $CO_2$ gas through the gas sample and measuring the amount of IR radiation absorbed as an indication of a concentration of $CO_2$ gas in the gas sample.

The concentration of $O_2$ gas in the gas sample is determined by transmitting light of wavelengths that will excite secondary phosphorescent light emission from a phosphorescent material within a gas sample cell and measuring the amount of phosphorescent light quenched by $O_2$ as an indication of the concentration of $O_2$ gas in the gas sample.

The gas sample cell in one embodiment is so constructed that the respective beams of IR radiation and light for detecting oxygen being transmitted through the gas sample are oriented in substantially orthogonal directions with respect to each other to avoid any potential interference. However, other relative beam orientations may be utilized without interference if proper interference filters are provided for detecting the respective beams.

In one embodiment of the present invention a plurality of containers, such as soft drink bottles containing the liquid sample to be analyzed, are connected through a plurality of valves, fine-bore tubing and a switching mechanism to the input of the gas sample cell which has its output connected to a vacuum pump. This system enables a plurality of soft drink bottles and the liquid solutions therein to be rapidly analyzed for quality control purposes.

Further scope of applicability of the present invention will become apparent from the detailed description given subsequently. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitative of the present invention and wherein.

DESCRIPTION OF PREFERRED EMBODIMENTS

Figure 2:
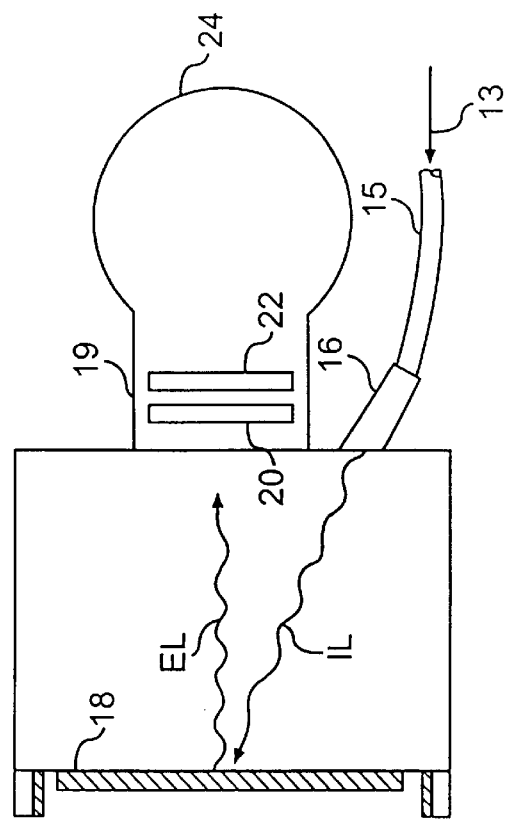
FIG. 2 is an end view of the gas sample cell and photomultiplier tube of FIG. 1.
Figure 1:
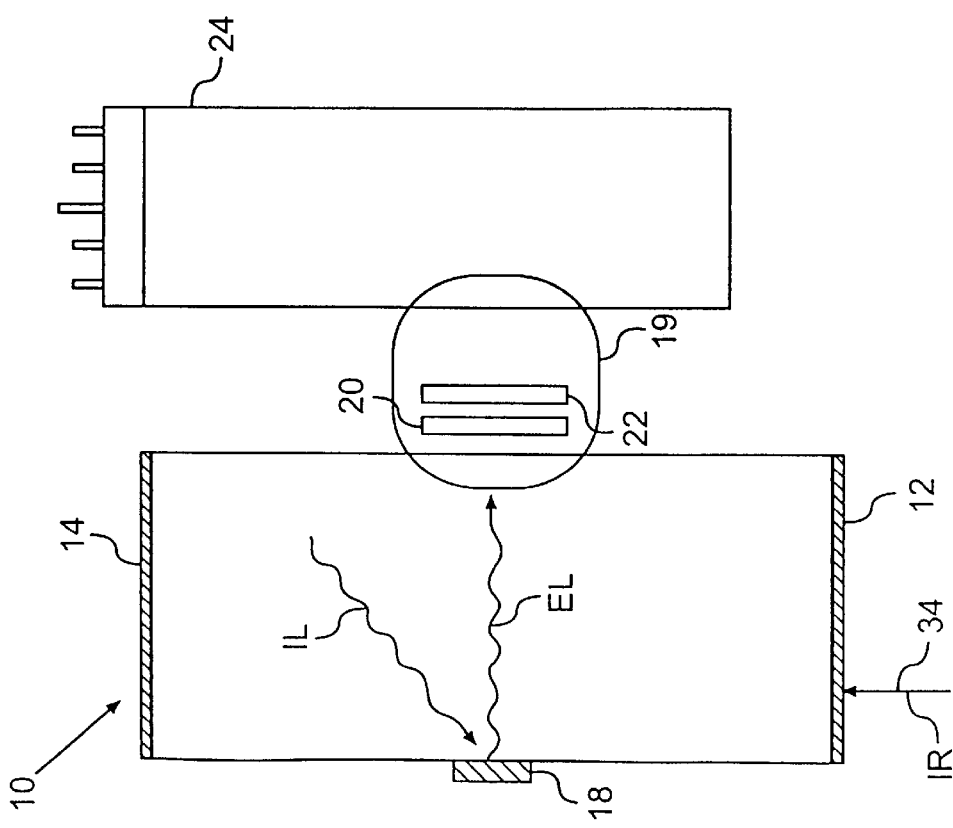
FIG. 1 is a top plan view of a gas sample cell according to the present invention coupled to a photomultiplier tube (PMT)
Figure 3:
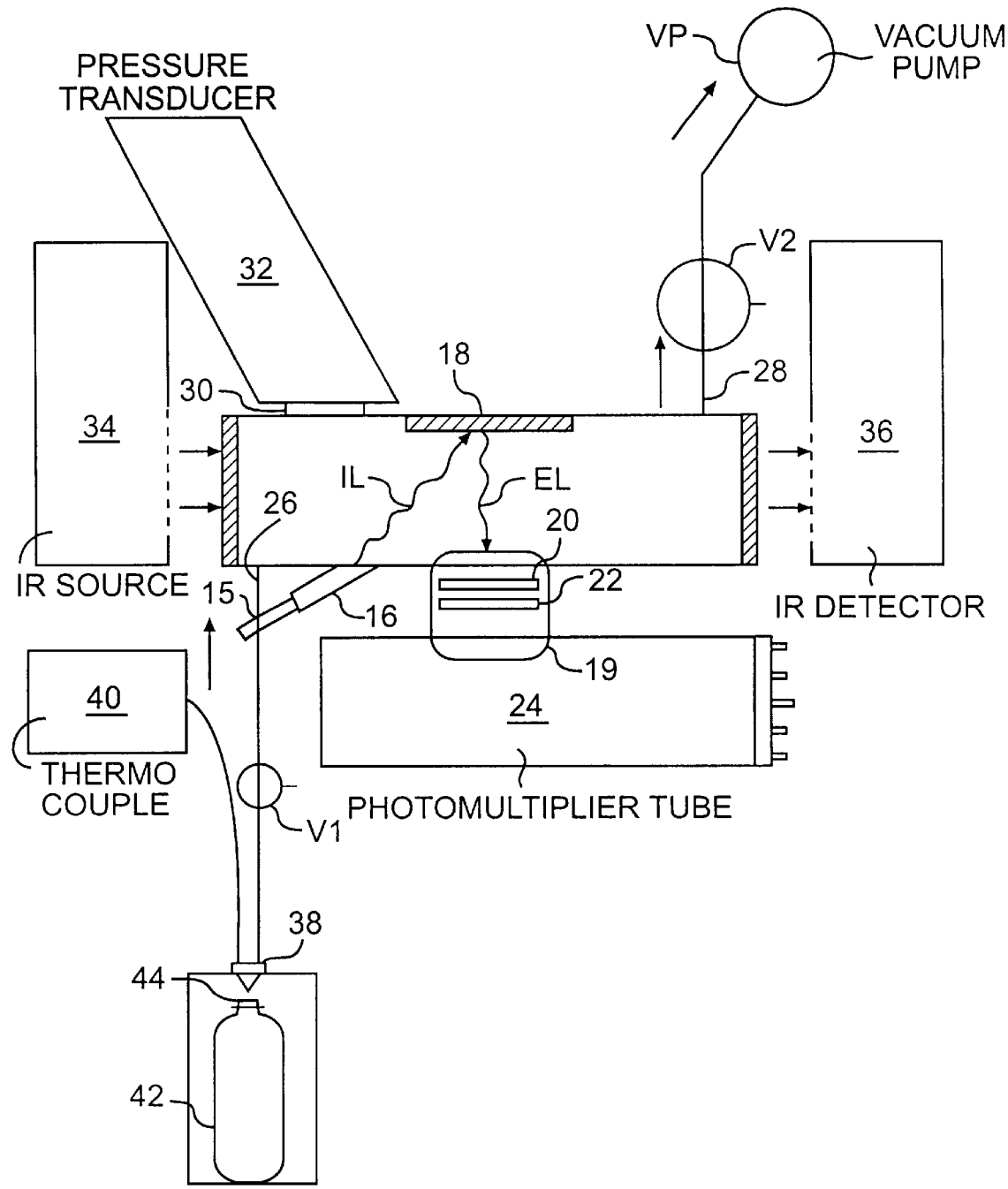
FIG. 3 is a diagrammatic view illustrating the overall system of the present invention for extracting a gas sample from a liquid sample in a beverage container and measurement of the quantities of $CO_2$, $O_2$ and $N_2$ gases in the extracted sample.

Referring collectively to FIGS. 1 to 3, there is illustrated a gas sample cell 10, including a hermetic housing, including an input window 12 for receiving IR radiation from an IR source 34, and an output window 14 for transmitting IR radiation, which has passed through the gas sample within the gas sample cell 10 to an IR detector 36. This portion of the system, which will be described further subsequently determines the amount of $CO_2$ (carbon dioxide) gas in the gas sample.

Gas sample cell 10 also includes an input conduit 16, slightly angled with respect to the longitudinal axis of the sample cell 10, for receiving light through a fiberoptic cable 15, which is coupled to a light source 13. Light source 13 may be a diode laser which preferably emits light in the 300 to 400 nm range. The light entering through conduit 16 is transmitted through the gas sample to an opposed wall of the sample cell, which has a silicone membrane 18 disposed thereon. Silicone membrane 18 contains a phosphorescent material, including sensing beads of Al(III)-ferron, an ion exchanger in the presence of oxygen, and the appropriate wavelength of incident light IL (300 to 400 nm) introduced through conduit 16 directed into the membrane 18, which will phosphoresce and emit approximately 600 nm light in quantities proportional to the oxygen concentration in the gas sample. The $CO_2$, and $N_2$ gases will not react with the Al(III) ferron or adversely affect the measurement of oxygen concentration. This phenomena is known as phosphorescent quenching and is more fully described in "Evaluation of Some Immobilized Room-Temperature Phosphorescent Metal Chelates as Sensing Materials for Oxygen", *Analytical Chemistry*, 1994, Vol. 66, No. 6, pp. 836–840. (This article is incorporated herein by reference). The emitted light EL from the silicon membrane 18 passes back across the longitudinal axis of the gas sample cell 10 into an optical coupling 19, where it is filtered by a pair of interference filters 20, 22, to a photomultiplier detector (PMT). Interference filter 20 cuts off radiation which is less than 500 nm, and interference filter 22 cuts off radiation having wavelengths above 700 nm. Thus, photomultiplier detector 24 will detect radiation in the 600 nm range. The voltage output from the photomultiplier tube 24 will be proportional to the oxygen concentration within the gas sample which quenches the light emitted from membrane 18.

As illustrated in FIG. 3, the respective beam paths for the infrared (IR) beam and the light for detecting oxygen concentration pass along directions X and Y which are substantially orthogonal to each other. This avoids the potential for interference between the respective radiation beams utilized for determining $CO_2$ and oxygen concentration, respectively.

The gas sample cell 10 also includes a measurement port 30 to which is connected a pressure transducer 32. Pressure transducer 32 measures the total pressure within the gas sample cell 10.

Sample cell 10 also includes an input port 26 connected in fluid communication through a valve V1 to a gas extracting device 38. Gas extracting device 38 may be what is commonly called a Zahm and Nagel piercing device. The piercing device 38 for extracting a gas from the headspace over the liquid sample within a container 42, such as a soft drink bottle, pierces a cap 44 on the bottle and removes a gas sample from the headspace over the liquid therein. A thermocouple 40 is provided to measure the temperature of the extracted gas sample.

Gas sample cell 10 includes an output port 28 connected to a valve V2 which is, in turn, connected to a vacuum pump VP. The vacuum pump VP is utilized for purging all gas from sample cell 10 prior to the commencement of a test of a gas sample. This purging may be achieved by opening valve V2 while valve V1 is closed. Conversely, when a test is to be performed, valve V2 will be closed and valve V1 opened to permit an extracted gas sample to flow into gas sample cell 10.

The carbon dioxide concentration in the gas sample is measured by infrared absorption of either 2.7 or 2.0 micron wavelength light emitted from IR source 34. Any accurate infrared detection method, such as an infrared spectrometer or filtometer, is suitable. The light path for infrared absorption measurements, as stated previously, is substantially perpendicular to the light path for the oxygen measurement system.

The pressure transducer 32, attached to measurement port 30, will determine the total pressure of the gas sample. Nitrogen pressure can be accurately measured by subtracting the partial pressure of oxygen, as determined by photomultiplier tube 24, and the partial pressure of carbon dioxide, as determined by IR detector 36, in conjunction with the temperature of the gas sample. With the use of standard solubility tables, one can convert from partial pressures and temperature into concentrations of dissolved $CO_2$, $O_2$ and $N_2$ in the liquid. Thus by combining the measurements made by the thermocouple 40 (temperature), pressure transducer 32 (total pressure), photomultiplier tube 24 (partial pressure of $O_2$), and IR detector 36 (partial pressure of $CO_2$), the concentrations of dissolved $CO_2$, $O_2$ and $N_2$ in a liquid sample, such as the beverage in bottle 42, may be quickly and accurately determined.

Figure 4:
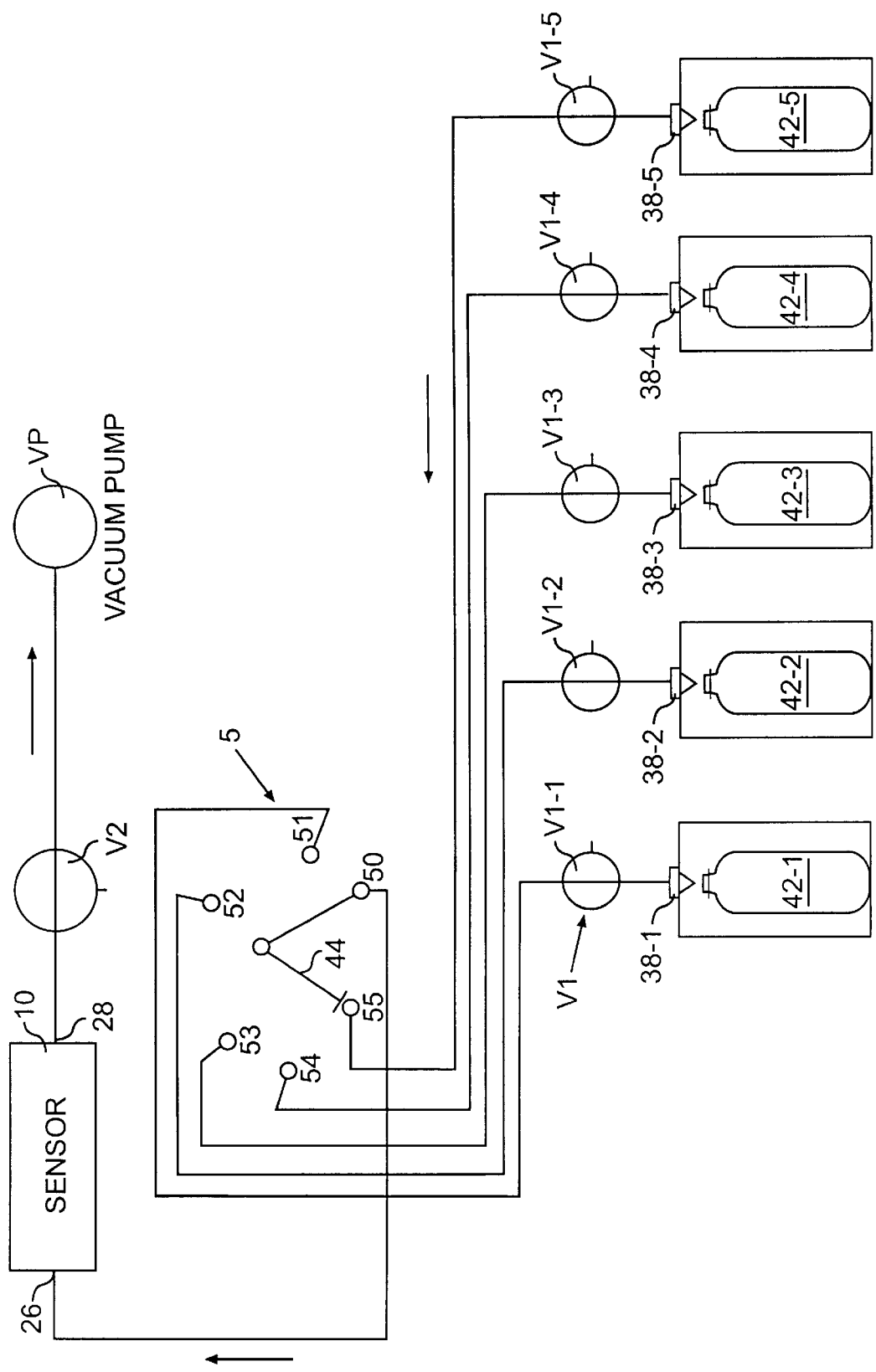
FIG. 4 is an embodiment of the present invention illustrating how the system of FIG. 3 can be applied to the detection of the gases of interest in a plurality of beverage containers connected to a common gas sample cell.

FIG. 4 illustrates how the gas sample cell 10 in the system of FIG. 3 may be utilized to test a plurality of beverage containers in a rapid and efficient manner. In FIG. 4 the number of beverage containers to be detected is five (5) for exemplary purposes only. It should be understood that more or fewer beverage containers may be tested in a similar manner as desired. As illustrated in FIG. 4 the five soft drink bottles are labeled 42-1 to 42-5. Each is associated with a suitable piercing device 38-1 to 38-5 which are in turn coupled to individual valves V1-1 to V1-5. These valves, referred to collectively as V1, are connected by suitable conduits to a series of ports 50, 51, 52, 53, 54, 55 in a rotary fluid handling valve 5. Depending on the position of the movable connecting arm 44, containers 42 are selectively connected to the input port 26 of gas sample cell 10. Thus, a batch of a plurality of liquid samples in containers 42 may be efficiently tested.

The operation of the method and apparatus of the present invention for simultaneously determining concentrations of $CO_2$, $O_2$ and $N_2$ dissolved in a liquid such as a soft drink within container 42 may be best understood by reference to FIG. 3. In a typical test scenario, valve V1 is closed and valve V2 is opened. Vacuum pump VP is then turned on to a evacuate sample cell 10 and remove an residual gas that may be present therein. Valve V2 is then closed, and the vacuum pump VP is turned off. At this point in time, background measurements for the presence of any residual $CO_2$ and $O_2$ can be determined by readings from photomultiplier tube 24 and IR detector 36, respectively. These measurements might be necessary if the pump did not evacuate below 0.2 psi.

A gas sample is then extracted from container 42 and the headspace therein by piercing device 38, which penetrates cap 44 on bottle 42. Valve V1 is then opened, and the bottle 42 is shaken to achieve equilibrium. This equilibrium may be monitored or checked using the pressure transducer 32.

Using the IR detector 36, the absorption of IR radiation from source 34, having wavelengths of approximately 2.7 microns (or other appropriate wavelengths that $CO_2$ absorbs), are determined. If necessary any background $CO_2$ previously measured may be subtracted out. The concentration of the carbon dioxide in the gas sample is determined by Beer's Law, wherein $A(v)=a(v)bc$, and $a(v)$ the absorbtivity, is a frequency-dependent molecular property. The value v is the path length through the sample cell 10, between the source 34 and the detector 36, and c is the concentration of $CO_2$.

Simultaneously the concentration and partial pressure of $O_2$ is determined using the voltage from photomultiplier tube 24. If necessary, any background oxygen signals previously detected are subtracted out to ensure an accurate reading.

Simultaneously, the temperature of the gas sample is measured by thermocouple 40, and this temperature will be utilized to convert $CO_2$ and $O_2$ concentrations to partial pressures.

Also simultaneously, the total pressure within gas sample cell 10 is measured by pressure transducer 32.

Then the partial pressures of $CO_2$ and $O_2$ are subtracted from the total pressure determined by transducer 32. This provides an approximate value for the partial pressure of nitrogen within the gas sample.

Then using standard solubility tables to convert from partial pressures and temperature into concentrations of dissolved $CO_2$, $O_2$ and $N_2$ in the liquid, these concentrations can be accurately determined. Of course a, suitable microprocessor can be utilized to calculate all relevant parameters.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for substantially simultaneously determining amounts of $CO_2$, $O_2$ and $N_2$ gases dissolved in a liquid sample, comprising the steps of:
    (a) evacuating a sample cell, including a phosphorescent material capable of being excited by primary light to emit secondary light, via vacuum pressure;
    (b) extracting a gas sample from the liquid sample, the extracted gas sample then entering the evacuated sample cell;
    (c) transmitting infrared (IR) radiation, at at least one wavelength absorbed by $CO_2$ gas, through the extracted gas sample in the sample cell;
    (d) transmitting primary light into the phosphorescent material in the sample cell;
    (e) measuring an amount of IR radiation absorbed as an indication of the concentration of $CO_2$ gas in the gas sample;
    (f) measuring, substantially simultaneous to step (e), an amount of secondary light emitted by the phosphorescent material, quenched by $O_2$ in the gas sample, as an indication of the concentration of $O_2$ gas in the gas sample, the transmitted IR radiation and emitted secondary light traveling through the sample cell in substantially orthogonal directions;
    (g) measuring the total pressure of the gas sample;
    (h) measuring the temperature of the gas sample;
    (i) determining the partial pressure of $CO_2$ gas from the absorbed amount of IR radiation measured in step (e) and the temperature measured in step (h);
    (j) determining the partial pressure of $O_2$ gas from the amount of emitted secondary light measured in step (f) and the temperature measured in step (h);
    (k) subtracting the sum of the partial pressures of $CO_2$ and $O_2$ determined in steps (i) and (j) from the total pressure measured in step (g) to determine the partial pressure of $N_2$; and
    (l) determining the concentration of $CO_2$, $O_2$ and $N_2$ gases dissolved in the liquid sample from the respective partial pressures determined in steps (i), (j) and (k) and the temperature measured in step (h).

2. The method of claim 1, wherein said transmitted primary light is in a range of about 300 to 400 nm, said emitted secondary light is about 600 nm, and said phosphorescent material is Al(III) ferron.

3. An apparatus for substantially simultaneously determining amounts of $CO_2$, $O_2$ and $N_2$ gases dissolved in a liquid sample, comprising:
    a sample cell including a phosphorescent material capable of being excited by primary light to emit secondary light;
    vacuum means for evacuating the sample cell via vacuum pressure;
    gas extracting means for extracting a gas sample from the liquid sample, the extracted gas sample then entering the sample cell;
    first transmitting means for transmitting infrared (IR) radiation, at at least one wavelength absorbed by $CO_2$ gas, through the extracted gas sample in the sample cell;
    second transmitting means for transmitting primary light into the phosphorescent material in the sample cell;
    first measuring means for measuring an amount of IR radiation absorbed as an indication of the concentration of $CO_2$ gas in the gas sample;
    second measuring means for substantially simultaneously measuring an amount of secondary light emitted by the phosphorescent material, quenched by $O_2$ in the gas sample, as an indication of the concentration of $O_2$ gas in the gas sample,the transmitted IR radiation and emitted secondary light traveling through the sample cell in substantially orthogonal directions;
    third measuring means for measuring the total pressure of the gas sample;
    fourth measuring means for measuring the temperature of the gas sample;
    calculation means for calculating the partial pressure of $CO_2$ gas from the measured amount of IR radiation absorbed and the measured temperature, for calculating the partial pressure of $O_2$ gas from the measured amount of secondary light and the measured temperature, and for calculating the partial pressure of $N_2$ by subtracting the sum of the calculated partial pressures of $CO_2$ and $O_2$ gas from the measured total pressure; and
    determination means for determining the concentration of $CO_2$, $O_2$ and $N_2$ gases dissolved in the liquid sample from the respective calculated partial pressures and the measured temperature.

4. The apparatus of claim 3 wherein said transmitted primary light is in a range of about 300 to 400 nm, said emitted secondary light is about 600 nm, and said phosphorescent material is Al(III) ferron.

5. The apparatus of claim 3 wherein a container with a cap thereon contains the liquid sample and said extracting means includes piercing means for piercing said cap to extract the gas sample from a headspace of the container, above the liquid sample.

6. The apparatus of claim 5 further including:
a first conduit, connecting said piercing means to said sample cell;
first valve in said first conduit;
a vacuum pump;
a second conduit connecting said vacuum pump to said sample cell; and
second valve in said second conduit.

7. The apparatus of claim 6 wherein said first valve, includes a plurality of valve assemblies connected to a plurality of said piercing means by a plurality of said first conduits, the plurality of piercing means being connected to a Plurality of containers.

8. The apparatus of claim 7 wherein said plurality of valve assemblies are individually operable.

* * * * *

UNITED STATES PATENT AND TRADEMARK OFFICE
CERTIFICATE OF CORRECTION

PATENT NO. : 6,138,497
DATED : October 31, 2000
INVENTOR(S) : John A. Nix et al.

Page 1 of 1

It is certified that error appears in the above-identified patent and that said Letters Patent is hereby corrected as shown below:

Column 6, claim 3,
Line 40, "sample,the" should read -- sample, the --.

Column 6, claim 5,
Line 64, after "claim3", insert a comma.

Column 8, claim 7,
Line 1, after "claim 6", insert a comma.
Line 1, after "first valve", delete the comma.
Line 5, "Plurality" should read -- plurality --.

Signed and Sealed this

Twenty-sixth Day of February, 2002

Attest:

JAMES E. ROGAN
Attesting Officer
Director of the United States Patent and Trademark Office